United States Patent [19]

Ohba et al.

[11] Patent Number: 4,980,082
[45] Date of Patent: Dec. 25, 1990

[54] FERROELECTRIC SMC LIQUID CRYSTAL COMPOSITION WHICH COMPRISES PYRIMIDINYLPHENYL ESTER COMPOUNDS

[75] Inventors: Kazumasa Ohba; Hiroshi Nonoguchi, both of Hyogo; Masaaki Taguchi; Takamasa Harada, both of Tokyo, all of Japan

[73] Assignees: Seiko Instruments Inc.; Teikoku Chemical Industry Co., Ltd., both of Japan

[21] Appl. No.: 91,660

[22] Filed: Sep. 1, 1987

[30] Foreign Application Priority Data

Sep. 2, 1986 [JP] Japan .................. 61-206513
Sep. 2, 1986 [JP] Japan .................. 61-206514

[51] Int. Cl.$^5$ ............... C07D 239/26; C09K 3/34
[52] U.S. Cl. ................. 252/299.610; 514/256; 514/269; 544/298; 544/335
[58] Field of Search ............... 544/298, 335; 514/256, 514/269

[56] References Cited

U.S. PATENT DOCUMENTS

| | | | |
|---|---|---|---|
| 3,997,536 | 12/1976 | Boller et al. | 544/242 |
| 4,311,610 | 1/1982 | Zaschke et al. | 544/335 |
| 4,462,923 | 7/1984 | Boller et al. | 252/299.61 |
| 4,725,688 | 2/1988 | Taquchi | 544/298 |

FOREIGN PATENT DOCUMENTS

| | | |
|---|---|---|
| 025119 | 3/1981 | European Pat. Off. |
| 0084194 | 7/1983 | European Pat. Off. |
| 225195 | 6/1987 | European Pat. Off. |
| 2257588 | 6/1973 | Fed. Rep. of Germany |
| 3518734 | 11/1986 | Fed. Rep. of Germany ...... 544/335 |

OTHER PUBLICATIONS

March, *Advanced Organic Chemistry*, 1979, pp. 86-89.

Primary Examiner—Mary C. Lee
Assistant Examiner—Zinna Northington-Davis
Attorney, Agent, or Firm—Bruce L. Adams; Van C. Wilks

[57] ABSTRACT

This invention relates to new optically active pyrimidinylphenyl ester compounds, having a liquid crystal phase of cholesteric and/or smectic C* phase, of the formula:

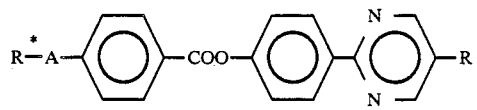

wherein R* represents an optically-active alkyl group having an asymmetric carbon atom which is

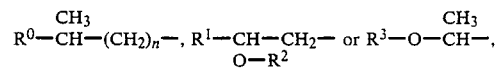

where $R^0$ is a straight chain alkyl group of 2 to 6 carbon atoms, $R^1$ is a straight chain alkyl group of 1 to 5 carbon atoms, $R^2$ is a straight chain alkyl group of 1 to 2 carbon atoms, $R^3$ is a straight chain alkyl group of 1 to 6 carbon atoms and n is 0 or 1, R presents a straight-chain alkyl group of 7 or 8 carbon atoms or a straight-chain alkoxy group of 7 or 8 carbon atoms and A represents

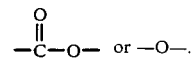

27 Claims, No Drawings

FERROELECTRIC SMC LIQUID CRYSTAL COMPOSITION WHICH COMPRISES PYRIMIDINYLPHENYL ESTER COMPOUNDS

BACKGROUND OF THE INVENTION

The present invention provides new liquid crystal compounds. In particular, the present invention provides liquid crystal compounds to be blended in a ferroelectric liquid crystal compound or composition to improve the properties thereof. The compounds of the present invention are usable in display elements or display devices, utilizing the electro-optical effects of the liquid crystal compounds.

(S)-2-Methylbutyl p-(p-n-decyloxybenzylideneamino)-cinnamate (DOBAMBC) is known as a ferroelectric liquid crystal compound. This Schiff base compound has been studied as a ferroelectric liquid crystal and various compounds have been prepared as the result. Known examples of these compounds are those of the general formula:

$$C_nH_{2n+1}O-\bigcirc-CH=N-\bigcirc-CH=\underset{X}{C}-COOCH_2\overset{*}{\underset{Y}{CH}}-CH_3$$

wherein X represents H, Cl or CN, Y represents Cl or $C_2H_5$ and * represents an asymmetric carbon atom.

However, the use of these compounds is limited, since the temperature at which they are in chiral smectic phase is higher than the room temperature and the chemical stability of them is low because they contain a Schiff base. Compounds of the structural formula:

$$C_nH_{2n+1}-\bigcirc-N=CH-\bigcirc-O-(CH_2)_m-\overset{*}{\underset{CH_3}{CH}}-C_2H_5$$
$$\qquad\qquad\qquad\underset{HO}{\diagdown\diagup}$$

were proposed as compounds free of the above-described defects and attracted public attention.

Further, Zaschke Horst Stolle and Reinhard described various compounds of the formula:

$$C_mH_{2m+1}-COO-\bigcirc-\underset{N}{\overset{N}{\bigcirc}}-C_nH_{2n+1}$$

wherein m represents a number of 1 to 11 and n represents a number of 5 to 8, in Z. Chem. 1975, 15 (11), 441 to 3. U.S. Pat. No. 4,389,329 discloses compounds having a $$-\bigcirc-COO-\bigcirc-\underset{N}{\overset{N}{\bigcirc}}-$$

structure. However, neither ferroelectric chiral smectic liquid crystal compounds are disclosed therein nor a suggestion of them is given therein.

SUMMARY OF THE INVENTION

It is therefore an object of the present invention is to provide new liquid crystal compounds which may be blended in a ferroelectric liquid crystal compound or composition to improve the properties thereof.

It is another object of this invention to provide a ferroelectric crystal composition having a wide range phase transition temperature, including room temperature, and a high speed response to an electric field.

DETAILED DESCRIPTION OF THE INVENTION

The compounds provided by the present invention are represented by the general formula:

$$R^*-A-\bigcirc-COO-\bigcirc-\underset{N}{\overset{N}{\bigcirc}}-R \qquad (I)$$

wherein R* represents an optically active alkyl group or an optically active alkoxyalkyl group having an asymmetric carbon atom, R represents a straight-chain alkyl group or a straight-chain alkoxy group and A represents $$\overset{O}{\underset{\|}{-C}}-O- \text{ or } -O-.$$

The compounds of the above general formula (I) are prepared by reacting a compound of the formula (II):

$$HO-\bigcirc-\underset{N}{\overset{N}{\bigcirc}}-R \qquad (II)$$

wherein R is as defined above, with a compound of the formula (III):

$$R^*-A-\bigcirc-COOH \qquad (III)$$

Wherein R* or A is as defined above, or a reactive derivative thereof.

The substituents R of the compounds of the formula (II) used herein are each a straight-chain alkyl or alkoxy group such as a pentyl, hexyl, heptyl, octyl, nonyl, decyl, undecyl, dodecyl, pentyloxy, hexyloxy, heptyloxy, nonyloxy, decyloxy, undecyloxy or dodecyloxy group.

Examples of the substituents R* in the formula (III) are (S)- or (R)-1-methylpropyl, (S)- or (R)-1-methylbutyl, (S)- or (R)-2-methylbutyl, (S)- or (R)-1-methylpentyl, (S)- or (R)-2-methylpentyl, (S)- or (R)-3-methylpentyl, (S)- or (R)-1-methylhexyl, (S)- or (R)-2-methylhexyl, (S)- or (R)-3-methylhexyl, (S)- or (R)-1-methylheptyl, (S)- or (R)-2-methylheptyl, (S)- or (R)-3-methylheptyl, (S)- or (R)-4-methylheptyl, (S)- or (R)-4-methylheptyl, and (S)- or (R)-5-methylheptyl. Appropriate compounds from the foregoing list ranging from methylpropyl to methylheptyl may be conveniently expressed by

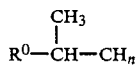

wherein $R^0$ is a straight chain alkyl group of 2 to 6 carbon atoms, and n is 0 or 1.

Other examples of the substituents R* are each an optically active alkyl group having an asymmetric carbon atom, of the formula:

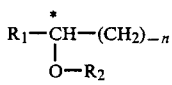

wherein $R_1$ represents an alkyl group having 1 to 5 carbon atoms, $R_2$ represents an alkyl group having 1 to 4 carbon atoms, n represents an integer and one of the elements directly bonded with the active carbon atom is an oxygen atom.

The configuration around the C* atom is either (S) or (R). Examples of the substituents R* include (S)- or (R)-2-methoxybutyl, (S)- or (R)-2-ethoxybutyl, (S)- or (R)-2-propoxybutyl, (S)- or (R)-2-butoxybutyl, (S)- or (R)-2-methoxypropyl, (S)- or (R)-2-ethoxypropyl, (S)- or (R)-3-methoxybutyl, (S)- or (R)-3-ethoxybutyl, (S)- or (R)-3-methoxypentyl and (S)- or (R)-3-ethoxypentyl groups.

Other examples of the substituents R* have the formula:

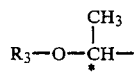

Wherein $R_3$ represents a straight-chain alkyl group having 1 to 6 carbon atoms.

The configuration around the C* atom is either (S) or (R). Examples of the substituents R* include (S)- or (R)-1-methoxyethyl, (S)- or (R)-1-ethoxyethyl, (S)- or (R)-1-propoxyethyl, (S)- or (R)-1-butoxyethyl, (S)- or (R)-1-pentyloxyethyl, or (S)- or (R)-1-hexyloxyethyl. Both starting compounds are dissolved in a suitable solvent (such as ethyl acetate, methyl acetate, ethyl ether, tetrahydrofuran, dioxane, dimethylformamide, dimethyl sulfoxide or ethylene glycol dimethyl ether) and the reaction is conducted in the presence of a condensing agent such as N,N'-dicyclohexylcarbodiimide, thionyl chloride or phosphorus oxychloride. The reaction proceeds smoothly when also a tertiary amine such as 4-dimethylaminopyridine, dimethylaniline or triethylamine is used.

Examples of the reactive derivatives of the compounds of the formula (III) include acyl halides (such as acyl chlorides formed by the reaction with thionyl chloride), active esters (such as those formed with p-nitrophenol) and mixed acid anhydrides (such as those formed with ethoxycarbonyl chloride). The reactive derivatives are subjected to the reaction in the presence of the tertiary amine. The compound (II) used as the starting material is prepared from β-dimethylamino-α-(n-alkyl or alkoxy)acrolein and hydroxybenzamidine.

The compound

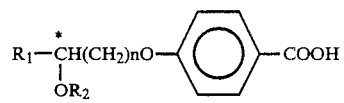

is prepared from optically active lactic acid. In particular, lactic acid is chemically modified repeatedly to modify the number n, for example, as follows:

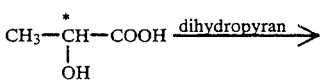

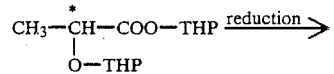

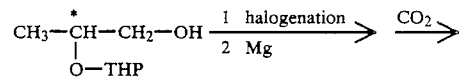

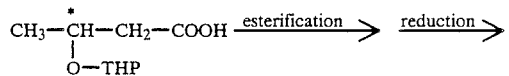

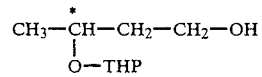

The above-mentioned cycle is repeated to increase the number of carbon atoms one by one. Thus, an optically active alcohol having a number n increased one by one is obtained. A reactive derivative such as that of the formula:

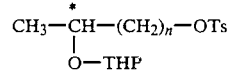

is derived from the product. The derivative is reacted with hydroxyphenyl benzoate to remove the pyranyl group. Then, the hydroxyl group is alkylated with an alkyl halide ($R_2X$). After hydrolysis, a compound of the formula:

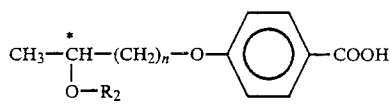

is obtained.

A compound of the formula

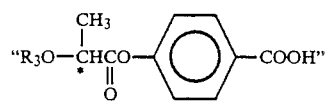

is obtained by following procedure using

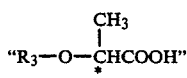

a starting material.

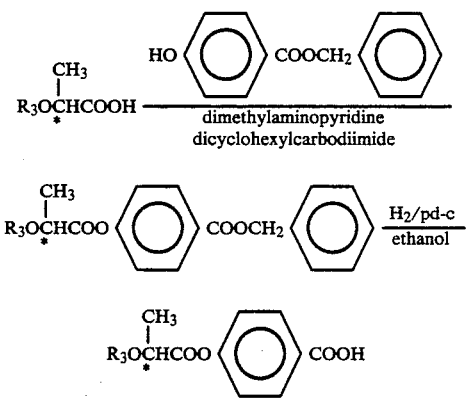

The starting compounds used in the present invention are prepared in a manner as will be described in referential examples given below.

The liquid crystal compounds of the present invention are in the cholesteric phase over a wide temperature range and many of them are not in the ferro-electric chiral smectic phase. The temperature range of the mixture of ferroelectric liquid crystal compounds in which the liquid crystal compounds of the present invention are present can be widened. Also the response characteristic and domain condition can be improved by blending the compound with a ferroelectric liquid crystal compound or composition.

The following examples will further illustrate the present invention.

EXAMPLE 1

Preparation of (S)-2-{4'-[4''-(2-methyl)butyryloxy]-benzoyloxy}phenyl-5-n-octyloxypyrimidine:

2.2 g (0.0099 mol) of (S)-4-(2-methyl)butyryloxybenzoic acid and 3.0 g (0.010 mol) of 2-(4-hydroxy)phenyl-5-n-octyloxypyrimidine were dissolved in 25 ml of ethyl acetate. 2.3 g (0.011 mol) of N,N'-dicyclohexylcarbodiimide and 0.12 g (0.098 mmol) of 4-dimethylaminopyridine were added to the solution and the mixture was stirred at room temperature for 7 h. After completion of the reaction, the reaction mixture was poured into ice-water and the organic layer was separated. After extraction with ethyl acetate followed by washing with a 10% aqueous sodium hydroxide solution, then with water and finally with a saturated aqueous common salt solution, the product was dried over magnesium sulfate and concentrated. The obtained product was purified according to silica gel column chromatography and recrystallized from ethanol to obtain 1.7 g of the intended compound.

$[\alpha]_D^{25} = +9.90°$ (C=2.19, CHCl$_3$)

IR$\gamma_{max}$ cm$^{-1}$: 1760, 1740, 1445, 1270, 1205, 1160, 1080, 885, 785

'H-NMR (CDCl$_3$, 60 MHz) δ(ppm):

| 0.67~2.13 | (m, 25H) |
| 2.33~2.90 | (m, 1H) |
| 4.07 | (t, 2H) |
| 7.21 | (d, 2H) |
| 7.29 | (d, 2H) |
| 8.23 | (d, 2H) |
| 8.37 | (s, 2H) |
| 8.42 | (d, 2H) |

The phase transition temperatures of the compound were as follows:

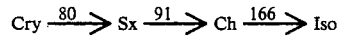

EXAMPLE 2

Preparation of (S)-2-{4'-[4''-(2-methyl)butyryloxy]-benzoyloxy}phenyl-5-n-octylpyrimidine:

1.5 g (0.0068 mol) of (S)-4-(2-methyl)butyryloxybenzoic acid, 2.0 g (0.0067 mol) of 2-(4-hydroxy)phenyl-5-n-octylpyrimidine, 1.5 g (0.0073 mol) of N,N'-dicyclohexylcarbodiimide, 80 mg (0.066 mmol) of 4-dimethylaminopyridine and 20 ml of ethyl acetate were reacted at room temperature for 10 h and then the same procedure as in Example 1 was repeated to obtain 1.1 g of the intended compound.

$[\alpha]_D^{25} = 10.2°$ (C=2.08, CHCl$_3$)

IR$\gamma_{max}$ cm$^{-1}$: 1760, 1735, 1430, 1270, 1200, 1165, 1075

'H-NMR (CDCl$_3$, 60 MHz) δ(ppm):

| 0.60~1.93 | (m, 2H) |
| 2.27~2.90 | (m, 3H) |
| 7.13 | (d, 2H) |
| 7.23 | (d, 2H) |
| 8.13 | (d, 2H) |
| 8.40 | (d, 2H) |
| 8.50 | (s, 2H) |

The phase transition temperatures of the compound were as follows:

EXAMPLE 3

Preparation of (S)-2-{4'-[4''-(2-methylbutoxy)phenylcarbonyloxy]phenyl}-5-n-octylpyrimidine:

1.6 g (0.0077 mol) of (S)-4-(2-methylbutoxy)benzoic acid and 2.3 g (0.0077 mol) of 2-(4-hydroxy)phenyl-5-n-octylpyrimidine were dissolved in 25 ml of ethyl acetate. 1.9 g (0.0092 mol) of N,N'-dicyclohexylcarbodiimide and 90 mg (0.074 mmol) of 4-dimethylaminopyridine were added to the solution and the mixture was stirred at room temperature for 17 h. After completion of the reaction, the reaction mixture was poured into ice-water and extracted with ethyl acetate. The extract was washed with 10% aqueous sodium hydroxide solution, then water and finally with a saturated aqueous common salt solution, dried over magnesium sulfate and concentrated. The product was purified according to silica gel column chromatography and then recrystallized from ethanol to obtain 1.3 g of the intended compound.

$[\alpha]_D^{25} = +5.4°$ (C=2.05, CHCl$_3$)

IR$\gamma_{max}$ cm$^{-1}$: 1735, 1610, 1435, 1260, 1200, 1165, 1080, 850, 655

$^1$H-NMR (CDCl$_3$, 60 MHz) δ(ppm):

| 0.63~2.17 | (m, 24H) |
|---|---|
| 2.58 | (t, 2H) |
| 3.82 | (d, 2H) |
| 6.89 | (d, 2H) |
| 7.26 | (d, 2H) |
| 8.03 | (d, 2H) |
| 8.41 | (d, 2H) |
| 8.52 | (s, 2H) |

The phase transition temperatures of the compound were as follows:

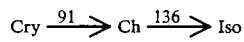

EXAMPLE 4

Preparation of (S)-2-{4'-[4''-(2-methylbutoxy)phenyl-carbonyloxy]phenyl}-5-n-octyloxypyrimidine:

The same procedure as in Example 1 was repeated except that 2.2 g (0.0083 mol) of (S)-4-(2-methylbutoxy)benzoic acid, 2.5 g (0.0083 mol) of 2-(4-hydroxy)phenyl-5-n-octyloxypyrimidine, 25 ml 0283 of ethyl acetate, 1.9 g (0.0092 mol) of N,N'-dicyclohexylcarbodiimide and 0.1 g (0.00082 mol) of 4-dimethylaminopyridine were used. 2.8 g of the intended compound was obtained.

$[α]_D^{25} = +5.0°$ (C=2.10, CHCl$_3$)

IRγ$_{max}$ cm$^{-1}$: 1740, 1605, 1435, 1280, 1250, 1190, 1170, 1080, 1050

$^1$H-NMR (CDCl$_3$, 60 MHz) δ(ppm):

| 0.50~2.16 | (m, 24H) |
|---|---|
| 3.78 | (d, 2H) |
| 4.03 | (t, 2H) |
| 6.87 | (d, 2H) |
| 7.27 | (d, 2H) |
| 8.07 | (d, 2H) |
| 8.32 | (d, 2H) |
| 8.35 | (s, 2H) |

The phase transition temperatures of the compound were as follows:

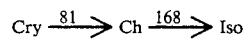

EXAMPLE 5

Preparation of 4-{1-(5-n-heptyl)pyrimidylphenyl}(S)-4-(2-methylbutyryloxy)benzoate:

2 g (0.0090 mol) of (S)-4-(2-methylbutyryloxy)benzoic acid, 2.4 g (0.0089 mol) of 2-(4-hydroxyphenyl)-5-n-heptylpyrimidine, 2.0 g (0.0097 mol) of N,N-dicyclohexylcarbodiimide and 0.11 g (0.00090 mol) of 4-dimethylaminopyridine were stirred in 30 ml of ethyl acetate at room temperature for 8 h.

The reaction mixture was poured into water and extracted with ethyl acetate. The extract was washed with water, dried and concentrated. After the purification according to silica gel column chromatography followed by the recrystallization from ethanol, 0.57 g of the intended compound was obtained.

$[α]_D^{25}$ +11.0 (C=2.06, CHCl$_3$)

IRγ$_{max}$ cm$^{-1}$: 1755, 1740, 1430, 1265, 1190, 1160, 1075

$^1$H-NMR (CDCl$_3$, 60 MHz) δ(ppm):

| 0.67~2.03 | (m, 18H) |
|---|---|
| 2.33~2.80 | (m, 3H) |
| 7.11 | (d, 2H) |
| 7.21 | (d, 2H) |
| 8.12 | (d, 2H) |
| 8.38 | (d, 2H) |
| 8.48 | (s, 2H) |

The phase transition temperatures of the compound were as follows:

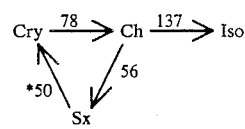

EXAMPLE 6

Preparation of S-(+)-4-(5-n-octyloxy-2-pyrimidinyl) phenyl 4'-(1-methylbutoxy) benzoic acid ester:

0.5 g of 4-(1-methylbutoxy) benzoic acid prepared from an optically active L-(−)-2-pentanol by standard methods and 0.721 g of 5-n-octyloxy-2-(4-hydroxyphenyl) pyridine were dissolved in 20 ml of dry ethyl acetate, and 0.495 g of N-N,-dicyclohexylcarbodiimide and 0.029 g of 4-dimethylaminopyridine were added to the solution. The mixture was allowed to react for one whole day at room temperature. After the reaction was completed, the insolube product was filterd out and the resultant product was extracted with ethyl acetate. The organic phase was washed with 2N hydrochloric acid, then, with 2% aqueous sodium hydroxide solution and finally with water and dried, and then the organic solvent was distilled off. The obtained product was subjected to silica gel chromatography and purified by recrystallization, 0.7 g of the intended compound was obtained The compound shows that the optical activity $[α]_D^{25}$ was +8.03 (C, 2.04 in CHCl$_3$)

IR γ$_{max}^{nujol}$ (cm$^{-1}$): 1742, 1610, 1585, 1560, 1528, 1280, 1255, 1210

$^1$H-NMR (CDCl$_3$ int TMS)

| (ppm) 8.44 | (s, 2H) |
|---|---|
| 8.43 | (d, 2H) |
| 8.24 | (d, 2H) |
| 7.29 | (d, 2H) |
| 6.94 | (d, 2H) |
| 4.60 | (t, 2H) |
| 4.49 | (m, 1H) |
| 1.31 | (d, 3H) |
| 0.53~2.16 | (m, 22H) |

The phase transition temperatures were as follows:

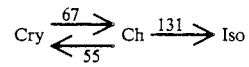

EXAMPLE 7

Preparation of R-(−)-4-(5-n-octyloxy-2-pyrimidinyl) phenyl 4'-(1-methylhepthyloxy) benzoic acid ester 0.8 g of 4-(1-methylohepthyoxy) benzoic acid prepared from an optically active D-(+)-2-octylalcohol by standard methods and 0.959 g of 5-n-octyloxy-2-(4- hydroxyphenyl) pyrimidine were dissolved in 20 ml of dry ethyl acetate, and 0.659 g of N, N'-dicyclohexylcarbodiimide and 36 mg of 4-dimethylaminopyridine were added to the solution, and then the reaction was conducted for one whole day at room temperature. After completion of the reaction, the reacted mixture was treated by standard methods. The obtained crude product was purified by column chromatography and recrystallization, 0.9 g of the intended compound was obtained the compound shows that the optical activity $[\alpha]_b^{25}$ was −2.54 (C, 2.005 in CHCl$_3$).

I.R. $\gamma_{max}^{nujol}$ (cm$^{-1}$): 1735, 1610, 1590, 1580, 1555, 1260, 1200, 1075, 1055

H'-NMR (CDCl$_3$)

| (ppm): | 8.44 | (s, 2H) |
|---|---|---|
| | 8.43 | (d, 2H) |
| | 8.14 | (d, 2H) |
| | 7.30 | (d, 2H) |
| | 7.94 | (d, 2H) |
| | 4.47 | (m, 1H) |
| | 4.07 | (t, 3H) |
| | 1.32 | (d, 3H) |
| | 0.56~2.1 | (m, 28H) |

The phase transition temperatures were as follows:

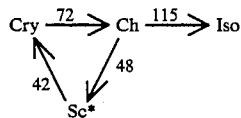

EXAMPLE 8

Preparation of (S)-2-{4'-[4''-(2-methoxy)butoxy]-benzoyloxyphenyl}-5-n-octyloxypyrimidine:

1.0 g (0.0045 mol) of (S)-4-(2-methoxybutoxy)benzoic acid and 1.34 g (0.0045 mol) of 2-(4-hydroxy)phenyl-5-n-octyloxypyrimidine were dissolved in 30 ml of ethyl acetate. 1.1 g (0.0053 mol) of N,N'-dicyclohexylcarbodiimide and 50 mg (0.041 mmol) of 4-dimethylaminopyridine were added to the solution and the reaction was conducted at room temperature for 7 h. After completion of the reaction, the reaction mixture was poured into water and extracted with ethyl acetate. The extract was washed with a 10% aqueous sodium hydroxide solution, then with water and finally with a saturated aqueous common salt solution, dried over magnesium sulfate and concentrated. The product was purified according to silica gel column chromatography and then recrystallized from ethanol to obtain 0.48 g of white crystals.

$[\alpha]_D^{25} = -12.0°$ (C 2.00, CHCl$_3$)

IR$\gamma_{max}$cm$^{-1}$: 1740, 1555, 1470, 1250, 1100, 1080, 885, 840, 780, 760

'H-NMR (CDCl$_3$, 60 MHz) δ(ppm):

| 0.66~2.07 | (m, 20H) |
|---|---|
| 3.27~3.70 | (s, 1H) |
| 3.43 | (s, 3H) |
| 3.90~4.23 | (m, 4H) |
| 6.93 | (d, 2H) |
| 7.27 | (d, 2H) |
| 8.10 | (d, 2H) |
| 8.37 | (d, 2H) |
| 8.40 | (s, 2H) |

The phase transition temperatures of the compound were as follows:

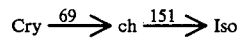

EXAMPLE 9

Preparation of (S)-2-{4'-[4''-(2-methoxy)butoxy]benzoyloxyphenyl}-5-n-octylpyrididine:

0.4 g (0.0018 mol) of (S)-4-(2-methoxy)butoxybenzoic acid, 0.54 g (0.0018 mol) of 2-(4-hydroxy)phenyl-5-n-octylpyrimidine, 10 ml of ethyl acetate, 0.41 g (0.002 mol) of N,N'-dicyclohexylcarbodiimide and 20 mg (0.016 mmol) of 4-dimethylaminopyridine were reacted at room temperature for 9 h and then the same procedure as in Example 1 was repeated to obtain 0.2 g of white crystals.

$[\alpha]_D^{25} = -12.9°$ (C 1.52, CHCl$_3$)

IR$\gamma_{max}$ cm$^{-1}$: 1745, 1610, 1430, 1260, 1200, 1165, 1080

'H-NMR (CDCl$_3$, 60 MHz) δ(ppm):

| 0.70~2.00 | (m, 20H) |
|---|---|
| 2.80~2.43 | (m, 2H) |
| 3.33~3.67 | (m, 1H) |
| 3.43 | (s, 3H, —OCH$_3$) |
| 4.03 | (d, 2H) |
| 6.94 | (d, 2H) |
| 7.20 | (s, 2H) |
| 7.27 | (d, 2H) |
| 8.10 | (d, 2H) |
| 8.43 | (d, 2H) |
| 8.55 | (d, 2H) |

The phase transition temperatures of the compound were as follows:

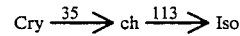

EXAMPLE 10

Preparation of (S)-2-{4'-[4''-(2-ethoxy)propoxy]benzoyloxyphenyl}-5-n-octyloxypyrimidine:

0.5 g (0.0022 mol) of (S)-4-(2-ethoxy)propoxybenzoic acid, 0.67 g (0.0022 mol) of 2-(4-hydroxy)phenyl-5-n-octyloxypyrimidine, 18 ml of ethyl acetate, 0.51 g (0.0025 mol) of N,N'-dicyclohexylcarbodiimide and 30 mg (0.025 mmol) of 4-dimethylaminopyridine were reacted at room temperature for 23 h and then the same procedure as in Example 1 was repeated to obtain 0.3 g of white crystals.

$[\alpha]_D^{25} = -11.0°$ (C 2.00, CHCl$_3$)

IR$\gamma_{max}$ cm$^{-1}$: 1740, 1470, 1450, 1250, 1080, 885, 780, 760

'H-NMR (CDCl$_3$, 60 MHz) δ(ppm):

| 0.50~2.13 | (m, 21H) |
|---|---|
| 3.42~3.90 | (m, 3H) |
| 3.90~4.30 | (m, 4H) |
| 6.90 | (d, 2H) |
| 7.28 | (d, 2H) |
| 8.13 | (d, 2H) |
| 8.41 | (d, 2H) |
| 8.42 | (s, 2H) |

The phase transition temperatures of the compound were as follows:

$$Cry \xrightarrow{59} ch \xrightarrow{143} Iso$$

EXAMPLE 11

A liquid crystal compound, i.e. (S)-2-{4'-[4''-(2-methoxy)propoxy]benzoyloxyphenyl}-5-n-octylpyrimidine, prepared in the same manner as in Examples 1 to 3 had the following phase transition temperatures:

$$Cry \underset{*36}{\overset{76}{\rightleftarrows}} ch \xrightarrow{136} Iso$$

EXAMPLE 12

Preparation of (s)-2-[4-{4'-(2-metoxy)propyonyloxy}benzoyloxy]phenyl-5-n-octylpyrimidine.

2.3 g (0.01 mol) of (s)-4-(2-metoxypropy-onyloxy) benzoic acid and 2.9 g (0.01 mol) 2-(4-hydroxy)phenyl-5-n-octylpyrimidine were dissolved in 25 ml of ethyl acetate, and 2.3 g (0.01 mol) of DCC and 0.13 g (0.0011 mol) of DMAP were added to the solution. The mixture was stirred for 26 hours at room temperature. After completion of the reaction, the precipitated product was filtered, and the filtrate was concentrated. The concentrated product was isolated according to silica gel column chromatography and then recrystallized from ethanol, yielding the intended compound. The yield was 0.28 g.

$[\alpha]_D^{25} = 31.1°$ (C=2.0, CHCl$_3$)

IR(nujol)γmax, cm$^{-1}$: 1780, 1740, 1435, 1270, 1200, 1165

H'-NMR (CDCl$_3$)

| (ppm) = | 0.50~2.00 | (m, 18H) |
|---|---|---|
| | 2.60 | (t, 2H) |
| | 3.47 | (s, 3H) |
| | 4.10 | (q, 1H) |
| | 7.23 | (d, 2H) |
| | 8.28 | (d, 2H) |
| | 8.20 | (d, 2H) |
| | 8.45 | (d, 2H) |
| | 8.57 | (s, 2H) |

The phase transition temperatures were as follows:

$$Cry \underset{46}{\overset{72}{\rightleftarrows}} Ch \xrightarrow{125} Iso$$

EXAMPLE 13

Preparation of (s)-2-[4-{4'-(2-butoxy)propyonyloxy}benzoyloxy]phenyl-5-n-octylpyrimidine.

1.5 g (0.0056 mol) of (s)-4-(2-butoxypropy-onyloxy) benzoic acid and 1.6 g (0.0056 mol) of 2-(4-hydroxy)-phenyl-5-n-octylpyrimidine were dissolved in 15 ml of ethyl acetate, and 1.3 g (0.0063 mol) of DCC and 0.07 g (0.00057 mol) of DMAP were added to the solution. Then, the mixture was stirred for 19 hours at room temperature and then the same procedure as in Example 12 was conducted to obtain 0.39 g of the intended compound. The yield was 0.39 g.

$[\alpha]_D^{25} = 30.2°$ (C=2, CHCl$_3$)

IR(nujol)γmax, cm$^{-1}$: 1780, 1735, 1470, 1440, 1265, 1200

H'-NMR (CDCl$_3$)

| (ppm) = | 0.63~2.07 | (m, 25H) |
|---|---|---|
| | 2.62 | (t, 2H) |
| | 3.53 | (t, 2H) |
| | 4.18 | (q, 1H) |
| | 7.23 | (d, 2H) |
| | 7.40 | (d, 2H) |
| | 8.22 | (d, 2H) |
| | 8.47 | (d, 2H) |
| | 8.57 | (d, 2H) |

The phase transition temperatures were as follows:

$$Cry \underset{26}{\overset{44}{\rightleftarrows}} Sc^* \xrightarrow{60} Ch \xrightarrow{96} Iso$$

EXAMPLE 14

Preparation of (s)-2-[4-{4'-(2-butoxy)propyonyloxy}benzoyloxy]phenyl-5-n-octyloxypyrimidine.

1.5 g (0.0056 mol) of (s)-4-(2-butoxypropyonyloxy) benzoic acid and 1.7 g (0.0056 mol) of 2-(4-hydroxy)-phenyl-5-n-octyloxypyrimidine were dissolved in 15 ml of ethyl acetate, and 1.3 g (0.0063 mol) of DCC and 0.07 g (0.00057 mol) of DMAP were added to the solution. The, the mixture was stirred for 15 hours at room temperature and then the same procedure as in Example 12 was conducted to obtain 0.33 g of the intended compound.

$[\alpha]_D^{25} = 27.8°$ (C=2.0, CHCl$_3$)

IR(nujol)γmax, cm$^{-1}$: 1780, 1750, 1470, 1450, 1275, 1205

H'-NMR (CDCl$_3$)

| f(ppm); | 0.63~2.00 | (m, 25H) |
|---|---|---|
| | 3.37~3.80 | (m, 2H) |
| | 4.08 | (t, 2H) |
| | 4.18 | (q, 1H) |
| | 7.23 | (d, 2H) |
| | 7.30 | (d, 2H) |
| | 8.25 | (d, 2H) |
| | 8.42 | (d, 2H) |
| | 8.43 | (s, 2H) |

The phase transition temperatures were as follows:

$$Cry \underset{60}{\overset{68}{\rightleftarrows}} Sc^* \xrightarrow{103} Ch \xrightarrow{138} Iso$$

The spontaneous polarization of this compound shows "positive" and the helix of Sc* phase is counterclockwise.

EXAMPLE 15

The compounds prepared in Examples 1, 2, 4, 8, 9 and 11 were blended in the following ferroelectric liquid crystal composition A and the properties of them were Composition A:

CH$_3$(CH$_2$)$_3$CH(CH$_3$)CH$_2$O—⟨phenyl⟩—⟨pyrimidine N,N⟩—OC$_8$H$_{17-n}$ 33.3 wt. %

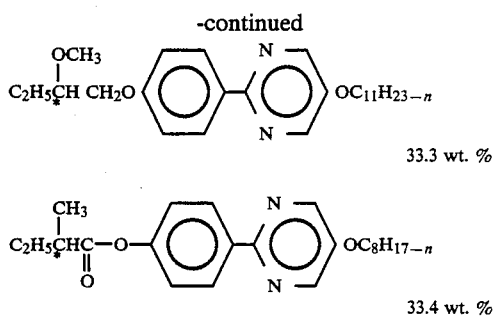

33.3 wt. %

33.4 wt. %

| Liquid crystal | Phase transition temperature | Response |
|---|---|---|
| Composition A | Cry —18→ Sc —*55→ SA —62→ Iso | 170 μs |
| Composition A + compound prepared in Example 1 (weight ratio: 5:1) | Cry —10→ Sc —*57→ SA —63→ Iso | 170 μs |
| Composition A + compound prepared in Example 2 (weight ratio: 4.6:1) | Cry —8→ Sc —*58→ Sa —65→ Iso | 180 μs |
| Composition A + compound prepared in Example 4 (weight ratio: 4:1) | Cry —−3→ Sx —7→ Sc —*59→ SA —66→ ch —68→ Iso | 190 μs |
| Composition A + compound prepared in Example 8 (weight ratio: 5:1) | Cry —6→ Sc —*57→ SA —67→ Ch —68→ Iso | 250 |
| Composition A + compound prepared in Example 9 (weight ratio: 5:1) | Cry —−4→ Sx —8→ Sc —*56→ SA —64→ Ch —65→ Iso | 180 |
| Compound A + compound prepared in Example 11 (weight ratio: 5:1) | Cry —−3→ Sx —9→ Sc —*57→ SA —65→ Ch —66→ Iso | 150 |

The response speed was determined in terms of the minimum pulse width necessary to cause switching of display patterns when the liquid crystal was poured into a cell of a clearance of 1.7 μm and pulses having various shapes were applied to the cell by varying the voltage from −20 to +20 V.

It can be understood from the above table that when a suitable amount of the compound of the present invention is blended in the composition A, the temperature range in which the Sc* phase is present can be widened in both upper and lower temperature sides. In addition, a composition having a Ch phase can be obtained as shown in the case of the blend of the composition A and the compound prepared in Examples 4, 8, 9 and 11.

It is also possible to increase the speed of response as observed in the blend of the composition A and the compound prepared in Examples 2 and 11.

REFERENTIAL EXAMPLE 1

Preparation of benzyl (S)-4-(2-methyl)butyryloxybenzoate:

4.5 g (0.044 mol) of (S)-2-methylbutyric acid and 10 g (0.044 mol) of benzyl 4-hydroxybenzoate were dissolved in 50 ml of ethyl acetate. 10 g (0.049 mol) of N,N′-dicyclohexylcarbodiimide and 0.54 g (0.44 mmol) of 4-dimethylaminopyridine were added to the solution and the mixture was stirred at room temperature for 18 h. After completion of the reaction, the reaction mixture was poured into water. The organic layer was separated, extracted with ethyl acetate and washed with a 10% aqueous sodium hydroxide solution, then with water and finally with a saturated aqueous common salt solution. The product was dried over magnesium sulfate and concentrated. The residue was purified according to silica gel column chromatography to obtain 9.3 g of the intended compound.

IR$\gamma_{max}$ cm$^{-1}$: 1760, 1720, 1610, 1510, 1270, 1210, 1180, 1100, 1020, 760, 700

$^1$H-NMR (CDCl$_3$, 60 MHz) δ(ppm):

| | |
|---|---|
| 0.82~1.42 | (m, 6H) |
| 1.42~2.02 | (m, 2H) |
| 2.33~2.80 | (m, 1H) |
| 5.28 | (s, 2H) |
| 7.06 | (d, 2H) |
| 7.32 | (s, 5H) |
| 8.02 | (d, 2H) |

REFERENTIAL EXAMPLE 2

Preparation of (S)-4-(2-methyl)butyryloxybenzoic acid:

9.0 g (0.029 mol) of benzyl (S)-4-(2-methyl)butyryloxybenzoate and 0.9 g of palladium/carbon were placed in 90 ml of ethanol to conduct catalytic reduction. After 1.5 h, an insoluble matter was filtered out and the filtrate was concentrated to obtain 6.3 g of crude intended compound.

IR$\gamma_{max}$ cm$^{-1}$: 3200~2450 (br), 1770, 1680, 1605, 1430, 1320, 1295, 1210, 1165, 1105, 760, 550

$^1$H-NMR (CDCl$_3$, 60 MHz) δ(ppm):

| | |
|---|---|
| 0.83~1.43 | (m, 6H) |
| 1.43~2.13 | (m, 2H) |
| 2.33~2.87 | (m, 1H) |
| 7.13 | (d, 2H) |
| 8.08 | (d, 2H) |
| 10.40 | (br, 1H) |

REFERENTIAL EXAMPLE 3

Preparation of (S)-4-(2-methyl)butyryloxybenzoic acid:

5 g (0.036 mol) of 4-hydroxybenzoic acid was dissolved in 30 ml of ethanol. 6 g (0.040 mol) of (S)-2-methylbutyl bromide and 15 ml of a 10% aqueous potassium hydroxide solution were added to the solution and the mixture was refluxed for 5 h. After completion of the reaction, the reaction mixture was acidified with hydrochloric acid to form precipitates. The precipitates were recovered by filtration, washed and dried to obtain 3.1 g of the intended compound.

REFERENTIAL EXAMPLE 4

Synthesis of 2-(4-hydroxy)phenyl-5-n-octylpyrimidine:

4.32 g of 4-hydroxybenzamidine hydrochloride and 5.7 g of $\beta$-dimethylamino-$\alpha$-n-octyloxyacrolein were dissolved in 40 ml of ethanol. 19.3 g of a 28% solution of sodium methylate in methanol was added to the solution and the mixture was refluxed for 8 h. After completion of the reaction, the reaction mixture was poured into ice-water, acidified with a dilute aqueous sulfuric acid solution and extracted with ethyl acetate The extract was washed with a saturated aqueous sodium hydrogencarbonate solution and then with a saturated aqueous common salt solution and concentrated to obtain 7.1 g of an oily product. It was recrystallized from n-hexane/ethanol to obtain 2.79 g of the intended compound.

IR$\gamma_{max}$ cm$^{-1}$: 3350~3050, 1610, 1595, 1435, 1280, 1245, 1175, 790

'H-NMR (CDCl$_3$, 60 MHz) $\delta$(ppm):

| | |
|---|---|
| 0.6~2.2 | (m, 17H) |
| 4.02 | (t, 2H) |
| 6.85 | (d, 2H) |
| 8.16 | (d, 2H) |
| 8.43 | (s, 2H) |

REFERENTIAL EXAMPLE 5

Preparation of (S)-ethyl 4-(2-tetrahydropyranyloxy)-butoxybenzoate:

5 g (0.030 mol) of ethyl 4-hydroxybenzoate was added to 1.6 g (0.033 mol) of 50% sodium hydride and 50 ml of dimethylformamide under stirring at room temperature. The mixture was stirred for 30 min. 9.9 g (0.030 mol) of (S)-2-tetrahydropyranyloxybutoxy p-toluenesulfonate was added thereto and the mixture was stirred at 80° C. for 10 h. Then, the mixture was poured into ice-water and extracted with ethyl acetate. The extract was washed with a 10% aqueous sodium hydroxide solution and then with a saturated aqueous common salt solution, dried and concentrated to obtain 8.8 g of the crude product.

IR$\gamma_{max}$ cm$^{-1}$: 1720, 1605, 1515, 1280~1250 (br), 1170, 1030, 770

REFERENTIAL EXAMPLE 6

Preparation of (S)-ethyl 4-(2-hydroxy)butoxybenzoate:

8.5 g (0.026 mol) of (S)-ethyl 4-(2-tetrahydropyranyloxy)butoxybenzoate was dissolved in 43 ml of ethanol. 0.2 g (0.0011 mol) of p-toluenesulfonic acid monohydrate was added to the solution and the mixture was refluxed for 3 h. Then, the reaction mixture was concentrated. Water was added thereto. After extraction with ethyl acetate, the extract was washed with water, dried over magnesium sulfate and concentrated. The product was purified according to silica gel column chromatography to obtain 3.4 g of white crystals.

IR$\gamma_{max}$ cm$^{-1}$: 3600~3200 (br), 1710, 1610, 1515, 1290~1230 (br), 1170, 1100, 850, 770

REFERENTIAL EXAMPLE 7

Preparation of (S)-ethyl 4-(2-methoxy)butoxybenzoate:

2.0 g (0.0084 mol) of (S)-ethyl 4-(2-hydroxy)butoxybenzoate was added to 0.44 g (0.0092 mol) of 50% sodium hydride and 15 ml of tetrahydrofuran under stirring at room temperature. 0.2 g (0.0011 mol) of hexamethylphosphoric triamide was added thereto. The mixture was stirred for 1 h. 1.43 g (0.01 mol) of methyl iodide was added thereto and the mixture was stirred at 40° C. for 1.5 h. After completion of the reaction, the reaction mixture was poured into ice-water and extracted with ethyl acetate. The extract was washed with a 10% aqueous sodium hydroxide solution, then with water and finally with a saturated aqueous common salt solution, dried over magnesium sulfate and concentrated to obtain 1.9 g of the crude product.

IR$\gamma_{max}$ cm$^{-1}$: 1710, 1605, 1515, 1280, 1250, 1170, 1100, 850, 770

REFERENTIAL EXAMPLE 8

Preparation of (S)-4-(2-methoxy)butoxybenzoic acid:

1.9 g (0.0075 mol) of S-ethyl 4-(2-methoxy)butoxybenzoate was dissolved in 10 ml of ethanol. 5 ml of a 10% aqueous sodium hydroxide solution was added to the solution. The mixture was stirred for 30 min, acidified with hydrochloric acid and extracted with ethyl acetate. The extract was washed with an aqueous sodium hydrogencarbonate solution, dried over magnesium sulfate and concentrated to obtain 1.9 g of an oily product. n-Hexane was added to the product to form crystals, which were filtered, washed with n-hexane and dried to obtain 1.2 g of the intended compound.

IR$\gamma_{max}$cm$^{-1}$: 3100~2500, 1680, 1605, 1430, 1300, 1255, 850, 770, 640

'H-NMR (CDCl$_3$, 60 MHz) $\delta$(ppm):

| | |
|---|---|
| 0.87~1.37 | (m, 3H) |
| 1.37~1.93 | (m, 2H) |
| 3.27~3.63 | (m, 1H) |
| 3.43 | (s, 3H) |
| 4.00 | (d, 2H) |
| 6.87 | (d, 2H) |
| 7.97 | (d, 2H) |
| 9.87 | (br, 1H) |

REFERENTIAL EXAMPLE 9

Preparation of (S)-ethyl 4-(2-tetrahydropyranyloxy)-propoxybenzoate:

1.0 g (0.021 mol) of 50% sodium hydride, 25 ml of dimethylformamide, 3.2 g (0.019 mol) of ethyl 4-hydroxybenzoate and 6.1 g (0.019 mol) of (S)-2-tetrahydropyranyloxypropoxy p-toluenesulfonate were reacted at 60° C. for 8 h. Then the same procedure as in Referential Example 1 was repeated to obtain 5.0 g of the crude product.

IR$\gamma_{max}$ cm$^{-1}$: 1715, 1610, 1280, 1255, 1170, 1120, 1035, 770

REFERENTIAL EXAMPLE 10

Preparation of (S)-ethyl 4-(2-hydroxy)propoxybenzoate:

A mixture of 4.5 g (0.014 mol) of (S)-ethyl 4-(2-tetrahydropyranyloxy)propoxybenzoate, 0.2 g (0.0011 mol) of p-toluenesulfonic acid monohydrate and 45 ml of methanol were refluxed for 1 h. Then the same procedure as in Referential Example 2 was repeated to obtain 2.2 g of the crude product.

IR$\gamma_{max}$ cm$^{-1}$: 3600~3200 (br), 1710 (br), 1610, 1515, 1300~1220 (br), 1170, 1100, 1030, 770

REFERENTIAL EXAMPLE 11

Preparation of (S)-4-(2-ethoxy)propoxybenzoic acid:

2.2 g (0.0098 mol) of (S)-ethyl 4-(2-hydroxy)propoxybenzoate and 0.2 g (0.0011 mol) of hexamethylphosphoric triamide were added to a mixture of 0.52 g (0.011 mol) of 50% sodium hydride and 15 ml of tetrahydrofuran under stirring. After 1 h, 1.8 g (0.012 mol) of methyl iodide was added thereto and the mixture was refluxed for 2 h. Then the mixture was poured into ice-water and extracted with ethyl acetate. The extract was washed with a 10% aqueous sodium hydroxide solution and then with a saturated aqueous common salt solution, dried over magnesium sulfate and concentrated. 20 ml of ethanol was added thereto to obtain a solution. The solution was refluxed together with a 10% aqueous sodium hydroxide solution for 1 h to conduct hydrolysis. After completion of the hydrolysis, the reaction mixture was poured into ice-water and extracted with ethyl acetate. After the same procedure as that described above, 1.4 g of an oily product was obtained. The product was purified according to silica gel column chromatography to obtain 0.76 g of the product.

$[\alpha]_D^{25} = -14.3°$ (C 1.05, CHCl$_3$)

IR$\gamma_{max}$ cm$^{-1}$: 3300~2400 (br), 1690, 1610, 1460, 1250, 1170, 850, 770

$^1$H-NMR (CDCl$_3$, 60 MHz) $\delta$(ppm):

|                     |
| ------------------- |
| 0.70~1.90 (m, 6H)   |
| 3.40~4.23 (m, 5H)   |
| 6.90 (d, 2H)        |
| 8.03 (d, 2H)        |
| 11.70 (br, 1H)      |

What is claimed is:

1. Pyrimidinylphenyl ester compounds having a cholesteric and/or smectic C* liquid crystal phase of the formula:

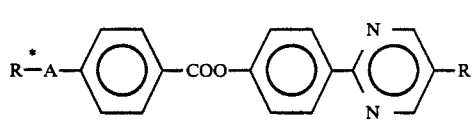

wherein R* represents an optionally active alkyl group having an asymmetric carbon atom which is

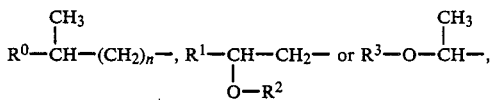

where R$^0$ is a straight chain alkyl group of 2 to 6 carbon atoms, R$^1$ is a straight chain alkyl group of 1 to 5 carbon atoms, R$^2$ is a straight chain alkyl group of 1 to 4 carbon atoms, R$^3$ is a straight chain alkyl group of 1 to 6 carbon atoms and n is 0 or 1, R represents a straight-chain alkyl group of 7 or 8 carbon atoms or a straight chain alkoxy group of 5 to 12 carbon atoms and A represents

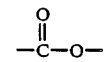

or —O—.

2. Pyrimidinylphenyl ester compounds having a cholesteric and/or smectic C* liquid crystal phase of the formula:

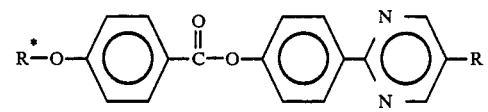

wherein R represents an alkyl or alkoxy group having a straight carbon chain of 7 or 8 carbon atoms and R* represents an optically active alkyl group having an asymmetric carbon atom which is

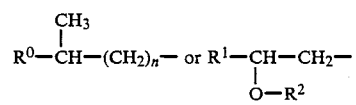

where R$^0$ is a straight chain alkyl group of 2 to 6 carbon atoms, R$^1$ is a straight chain alkyl group of 1 to 5 carbon atoms, R$^2$ is a straight chain alkyl group of 1 to 4 carbon atoms and n is 0 or 1.

3. Pyrimidinylphenyl ester compounds of the formula:

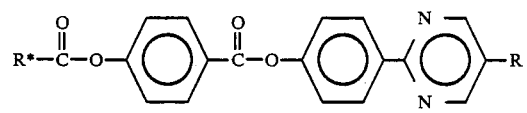

wherein R represents an alkyl or alkoxy group having a straight carbon chain of 5 to 12 carbon atoms R* represents an optically active alkyl group having an asymmetric carbon atom which is

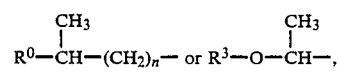

where R$_4$ is a straight chain alkyl group of 2 to 6 carbon atoms, and R$^3$ is a straight chain alkyl group of 1 to 6 carbon atoms and n is 0 or 1.

4. Pyrimidinylphenyl ester compounds of the formula:

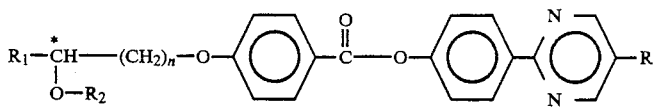

wherein R represents an alkyl or alkoxy group having a straight carbon chain of 5 to 12 carbon atoms, $R_1$ is a straight chain alkyl group having 1 to 5 carbon atoms, $R_2$ is a straight chain alkyl group having 1 to 4 carbon atoms and n is 1.

5. Pyrimidinylphenyl ester compounds of the formula:

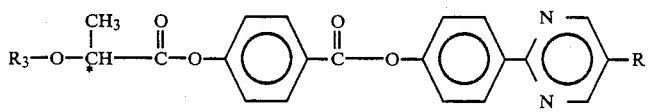

wherein R represents an alkyl or alkoxy group having a straight carbon chain of 5 to 12 carbon atoms, $R_3$ is a straight chain alkyl group having 1 to 6 carbon atoms.

6. A compound as defined in claim 3, wherein the compound is (S)-2-[4'-[4'''-(2-methyl)butyryloxy]-benzoyloxy]phenyl-5-n-octyloxypyrimidine.

7. A compound as defined in claim 3, wherein the compound is (S)-2-[4'-[4'''-(2-methyl)butyryloxy]-benzoyloxy]phenyl-5-n-octylpyrimidine.

8. A compound as defined in claim 2, wherein the compound is (S)-2-[4'-[4'''-(2-methylbutoxy)phenyl-carbonyloxy]phenyl]-5-n-octylpyrimidine.

9. A compound as defined in claim 2, wherein the compound is (S)-2-[4'-[4'''-(2-methylbutoxy)phenyl-carbonyloxy]phenyl]-5-n-octyloxypyrimidine.

10. A compound as defined in claim 3, wherein the compound is 4-[1-(5-n-heptyl)pyrimidylphenyl](S)-4-(2-methylbutyryloxy)benzoate.

11. A compound as defined in claim 2, wherein the compound is S-(+)-4-(5-n-octyloxy-2-pyrimidinyl)phenyl 4'-(1-methylbutoxy) benzoic acid ester.

12. A compound as defined in claim 2, wherein the compound is R-(−)-4-(5-n-octyloxy-2-pyrimidinyl)phenyl 4'-(1-methylheptyloxy) benzoic acid ester.

13. A compound as defined in claim 4, wherein the compound is (S)-2-[4'-[4''-(2-methoxy)butoxy]-benzoyloxyphenyl]-5-n-octyloxypyrimidine.

14. A compound as defined in claim 4, wherein the compound (S)-2-[4'-[4''-(2-methoxy)butoxy]-benzoyloxyphenyl]-5-n-octylpyrimidine.

15. A compound as defined in claim 4, wherein the compound is (S)-2-[4'-[4''-(2-ethoxy)propoxy]-benzoyloxyphenyl]-5-n-octyloxypyrimidine.

16. A compound as defined in claim 4, wherein the compound is (S)-2-[4'-[4''-(2-methoxy)propoxy-benzoyloxyphenyl]-5-n-octylpyrimidine.

17. A compound as defined in claim 5, wherein the compound is (S)-2-[4-[4'-(2-methoxy)propionyloxy]benzoyloxy]phenyl-5-n-octylpyrimidine.

18. A compound as defined in claim 5, wherein the compound is (S)-2-[4-[4'-(2-butoxy)propionyloxy]benzoyloxy]phenyl-5-n-octylpyrimidine.

19. A compound as defined in claim 5, wherein the compound is (S)-2-[4-[4'-(2-butoxy)propionyloxy]benzoyloxy]phenyl-5-n-octyloxypyrimidine.

20. A ferroelectric SmC* liquid crystal composition comprising at least one compound of the formula

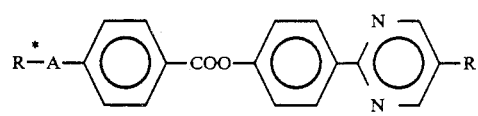

where R* represents an optically active alkyl group having an asymmetric carbon atom which is

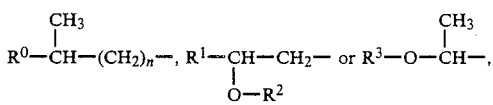

where $R^0$ is a straight chain alkyl group of 2 to 6 carbon atoms, $R^1$ is a straight chain alkyl group of 1 to 5 carbom atoms, $R^2$ is a straight chain alkyl group of 1 to 4 carbon atoms, $R^3$ is a straight chain alkyl group of 1 to 6 carbon atoms and n is 0 or 1, R represents a straight chain alkyl group of 7 or 8 carbon atoms or a straight-chain alkoxy group of 7 or 8 carbon atoms and A represents

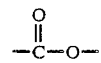

or —O—.

21. A composition as defined in claim 20, including a ferroelectric SmC* liquid crystal compound.

22. Compounds as defined in claim 1, wherein $R^1$ has 1 to 2 carbon atoms, $R^2$ has 1 to 2 carbon atoms, and $R^3$ has 1 to 4 carbon atoms.

23. Compounds as defined in claim 2, wherein $R^1$ has 1 to 2 carbon atoms and $R^2$ has 1 to 2 carbon atoms.

24. Compounds as defined in claim 3, wherein R has 7 or 8 carbon atoms, $R^0$ has 2 carbon atoms and $R^3$ has 1 to 4 carbon atoms.

25. Compounds as defined in claim 4, wherein R has 7 or 8 carbon atoms, $R_1$ has 1 to 2 carbon atoms, and $R_2$ has 1 to 2 carbon atoms.

26. Compounds as defined in claim 5, wherein R has 7 or 8 carbon atoms and $R_3$ has 1 to 4 carbon atoms.

27. A composition as defined in claim 20, wherein $R^1$ has 1 to 2 carbon atoms, $R^2$ has 1 to 2 carbon atoms, and $R^3$ has 1 to 4 carbon atoms.

* * * * *